United States Patent [19]

Robertson et al.

[11] Patent Number: 4,873,057

[45] Date of Patent: Oct. 10, 1989

[54] APPARATUS FOR CARRYING OUT A TITRATION PROCEDURE FOR THE CHEMICAL ANALYSIS OF A SAMPLE

[75] Inventors: Peter M. Robertson, Winkel b. Buelach; Erwin Suter, Zurich, both of Switzerland

[73] Assignee: Zellweger Uster Ltd, Uster, Switzerland

[21] Appl. No.: 27,001

[22] Filed: Mar. 10, 1987

[30] Foreign Application Priority Data

Mar. 11, 1986 [CH] Switzerland ............................ 994/86

[51] Int. Cl.$^4$ ............................................ G01N 31/16
[52] U.S. Cl. ...................................... 422/75; 422/103; 422/110; 422/114; 422/115; 436/51; 436/53; 436/163; 436/180
[58] Field of Search ................. 422/75, 103, 110, 114, 422/115; 436/51, 163, 53, 58, 180

[56]  References Cited

U.S. PATENT DOCUMENTS 3,717,435  2/1973  Ertl et al. ............................ 436/163
4,165,218  8/1979  Van Humbeeck et al. ...... 422/75 X
4,215,091  7/1980  Petersen et al. ...................... 422/75

Primary Examiner—Barry S. Richman
Assistant Examiner—Lynn M. Kummert
Attorney, Agent, or Firm—Burns, Doane, Swecker & Mathis

[57]  ABSTRACT

The sample and the reagent required for titration are fed into a titration vessel (1), the reagent and/or sample being supplied intermittently in the form of pulses of liquid. Toward this end, a controlled valve (9) is provided in the supply line (4) for the reagent. The opening and closing times of this valve (9) and, hence, the frequency and duration of the pulses of liquid, are chosen such that the ratio of the average sample flow to the average reagent flow is sufficient to achieve the ratio of sample to the reagent at the equivalence point. This renders continuous titration possible, for which only one pump (7) is needed, which does not require any complex servo system and, therefore, has a low energy consumption.

16 Claims, 2 Drawing Sheets

APPARATUS FOR CARRYING OUT A TITRATION PROCEDURE FOR THE CHEMICAL ANALYSIS OF A SAMPLE

BACKGROUND

The term "titration" is understood to mean the determination of the unknown content of an aqueous solution of an acid or base (the sample) by the addition of a base or acid solution (the reagent) of known concentration until an indicator undergoes a change in color. From the number of cubic centimeters and concentration (titer) of the base or acid consumed, the acid or base content of the solution titrated in this manner can then be readily calculated.

For titration under laboratory conditions, the known discontinuous titration procedure with pipettes and (optionally motor-driven) burettes is used. Since this procedure requires the constant presence of an operator, it is unsuitable for industrial use.

It has already been proposed to automate the discontinuous titration in order that it can also be used industrially. However, since considerable problems arise during the delivery of the sample and the reagent to the titration vessel, during the draining of the titrated solution from the titration vessel, and during the metering of the quantities of liquid, which, among other things, requires a large number of valves, this automated discontinuous titration has not gained acceptance. In addition, controls, which are expensive because of the valves, are necessary and the calculated titer must be stored from one titration to the next, for which additional devices are required.

Continuous titration procedures for industrial use are known, in which sample and reagent are fed into the titration vessel in a controlled and variable ratio. To do this, at least two adjustable pumps are necessary, the control of which requires expensive servo systems and which, in addition, consume a large amount of power.

SUMMARY OF THE INVENTION

The invention relates to a titration procedure for the chemical analysis of a sample, in which the sample is continuously mixed with a reagent and the equivalence point is determined by means of a suitable sensor which is itself known in the art.

The titration procedure of the invention is intended to permit the continuous determination of the concentration of a sample through a continuous titration procedure requiring neither two adjustable pumps, which consume a large amount of energy, nor expensive servo systems for their control.

According to the invention, this object is achieved in that the supply of reagent and/or sample to the titration vessel occurs intermittently in the form of pulses of liquid, the frequency and duration of these pulses of liquid being chosen such that the ratio of the average sample flow rate to the average reagent flow rate is sufficient to achieve the ratio of sample to reagent at the equivalence point.

The invention further relates to an apparatus for carrying out said titration procedure by means of a titration vessel that contains a sensor, and supply lines, which lead to the titration vessel, for feeding the sample and the reagent. These supply lines are characterized by a valve located in the line for feeding the reagent and/or in the line for feeding the sample, and by a control element assigned to this valve for controlling the opening and closing times of the valve for the purpose of adjusting said ratio of the average sample flow to the average reagent flow.

Due to the novel intermittent delivery of reagent and/or sample and to the novel selection of said ratio of the average sample flow to the average reagent flow, only one pump is needed for delivering the sample and the reagent, both flows being delivered continuously so that no servo system is required. The intermittent delivery is carried out by a controlled valve and the control of its opening and closing times and thereby the adjustment of this ratio of the average sample flow to the average reagent flow, is effected by a suitable control element, which is formed from simple electronic components.

BRIEF DESCRIPTION OF THE INVENTION

The invention will now be described in greater detail by reference to a practical embodiment shown in the drawings, in which:

FIG. 1 is a schematic representation of a titration apparatus incorporating the invention, and FIG. 2 are diagrams for explaining its operation.

DETAILED DESCRIPTION OF A PREFERRED EMBODIMENT

Figure 1:
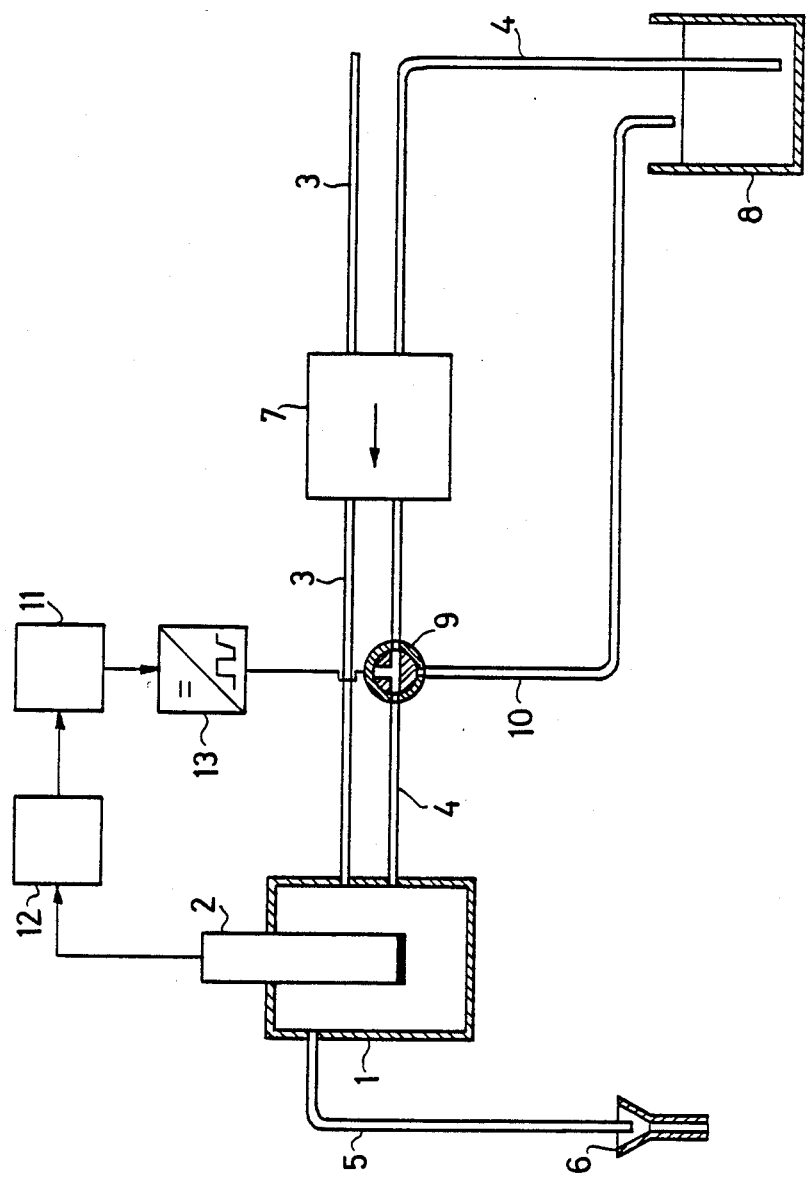

As shown in FIG. 1, the apparatus is comprised of a titration vessel 1 having a sensor 2 for determining the equivalence point of a titrated sample. The sample to be examined and the reagent are fed into titration vessel 1 via lines 3 and 4, respectively. Line 5 running into drain 6 serves to discharge the titrated solution from titration vessel 1.

The two lines 3 and 4 are passed through a pump system 7, preferably a peristaltic pump, with which the sample to be titrated and the reagent are delivered at a given delivery rate. The apparatus shown is especially suited for industrial applications, for example for the analysis of phosphatizing baths, where line 3 for the sample branches off from the production circuit and line 4 delivers the reagent from a reagent reservoir 8.

In order to control the ratio of the volumes of sample to reagent fed into titration vessel 1, a controlled valve 9 is located in line 4 between pump 7 and titration vessel 1. This valve could also be provided in line 3 instead of in line 4, or even in both lines. As shown in the drawing, valve 9 is a three-way valve, to the third outlet of which is connected line 10 for returning the reagent to reagent reservoir 8 when line 4 is closed. Needless to say that two two-way valves could also be used instead of a three-way valve 9. In that case, line 4 would have a branching downstream with respect to pump 7, from which a first branch with the first two-way valve would lead to reagent vessel 1 and a second branch with the second two-way valve would lead to reagent reservoir 8.

If valve 9 is opened and closed in a particular rhythm, i.e., operated in a particular duty ratio, an average reagent flow will result which is proportional to this duty ratio. Since the sample flow in line 3 is constant, the average sample flow in this line is also constant and, hence, sample and reagent are mixed in titration vessel 1 in a ratio which is proportional to this duty ratio of valve 9.

The duty ratio is controlled in such a way that the equivalence point is reached in titration vessel 1, and this is achieved by selecting the duty ratio such that the ratio of the average sample flow to the average reagent flow is sufficient to achieve the ratio of sample to reagent at the equivalence point.

The volume of the solution in titration vessel 1 is chosen to be so large that fluctuations in the concentration caused by the intermittent, pulse-like addition of the reagent are prevented or at least minimized to such a degree that the accuracy of the analysis is not impaired. In practice, it is sufficient for this purpose if the volume of titration vessel 1 is at least 10 times as large as the maximum reagent volume injected into titration vessel 1 with one pulse of liquid. In this connection, it may be mentioned that the opening time of valve 9 and, hence, the longest possible pulse of reagent, lasts no longer than 10 seconds, whereas the residence time of the actual titrated solution in titration vessel 1 is of the order of several minutes. In this way, the volume of titration vessel 1 smoothes out the variations in the supply of solutions and keeps the concentration in titration vessel 1 sufficiently constant. Thus, valve 9 is always opened only long enough so that the ratio of the two components in titration vessel 1 corresponds to their ratio at the equivalence point.

The control of three-way valve 9 is effected by means of a servo controller 11. This controller is preferably of the PID (proportional, integral, derivative) a P (proportional) or a PI (proportional, integral) type, although controller can also be used. The input of controller is connected via a measuring transmitter 12 to sensor 2, and its output is connected via a pulse-duration modulator 13 to valve 9. Sensor 2 is a conventional sensor for titrations, e.g., a pH electrode, a redox electrode, a photometer, and the like. The output signal of sensor 2 is transformed in a manner known in itself by measuring transmitter 12. By way of example, an impedance conversion or the generation of a standardized signal, takes place with temperature correction in the transmitter 12, and PID controller 11 compares the actual signal supplied by measuring transmitter 12 with a desired signal, and supplies to pulse-duration modulator 13 an analog signal which is proportional to the difference between the actual signal and the desired signal. In this case, the desired signal corresponds to the signal for the equivalence point of the particular sample concerned.

Pulse-duration modulator 13 now converts the analog signal of PID controller 11 into a corresponding digital signal, during which, for example, the leading edge of the digital signal opens valve 9 (referred to line 4), and the falling edge recloses it.

Figure 2:
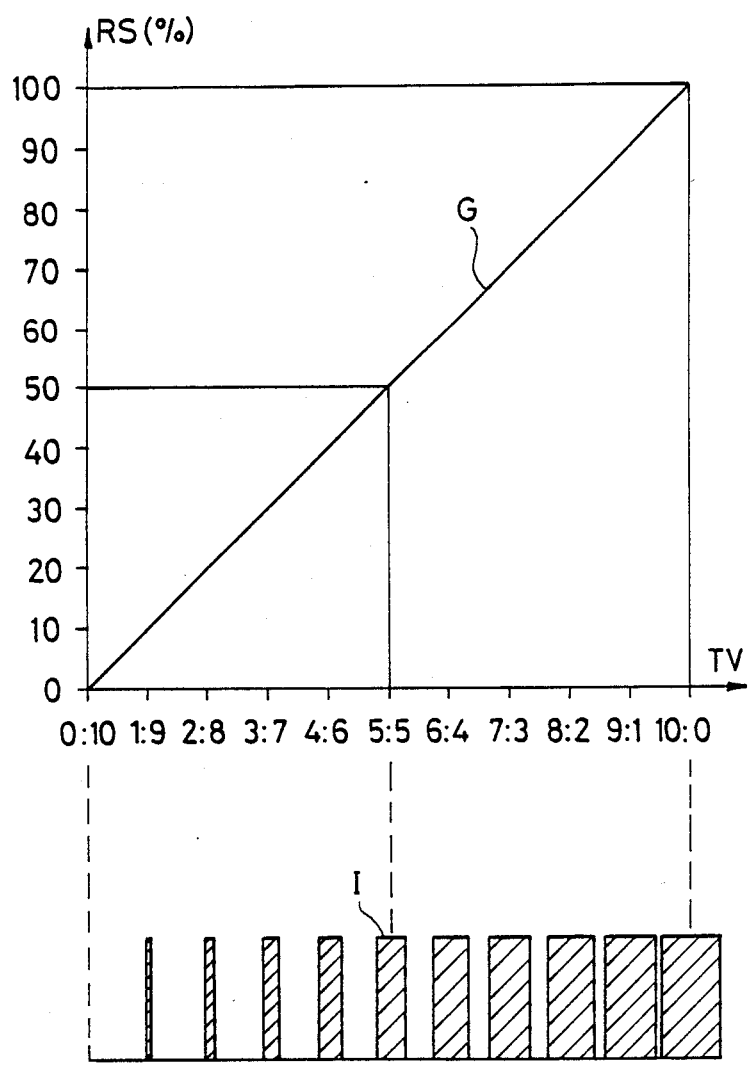

In FIG. 2, the ratios for determining the average reagent flow and for fixing the duty ratio of valve 9 are shown with reference to two diagrams. The upper diagram of this figure shows the relationship between the average reagent flow RS and duty ratio TV (on/off), and the lower diagram shows this duty ratio in another form of representation.

In the upper diagram of FIG. 2, the average reagent flow RS is plotted on the ordinate in percentage of throughput line 4. Here, 0% means that valve 9 is continuously closed, and 100% means that valve 9 is continuously open. At 100%, for example, identical volumes of reagent and sample would be fed into titration vessel 1 per unit time and, at 0%, no reagent at all. If the duty ratio TV of valve 9 is plotted on the abscissa and if, for example, a duration of 10 pulses is assumed for one complete closing and opening cycle of valve 9, then the ratio of valve open to valve closed at 0% is equal to 0:10 and, at 100%, it is equal to 10:0. For the relationship between the average reagent flow RS and the duty ratio TV, this produces the straight line G which has been plotted. Now, if the displaced volume in line 4 at 100% RS and the concentration of the reagent solution are known, one can calculate what percentage RS is required to reach the equivalence point for the titration. For example, if this value, as shown, is equal to 50%, a duty ratio of 5:5 is obtained for the operation of valve 9.

In the lower part of FIG. 2, the duty ratio is shown in terms of the effective on-and-off times of valve 9. Here, the shaded areas signify that valve 9 is switched on. In the case of the example chosen, in which RS=50% and TV=5:5, valve 9 would hence be open for one-half of a cycle, which corresponds to pulse I, and closed the other half. Accordingly, in terms of duration, pulse I corresponds to the output signal of pulse-duration modulator 13, the leading edge of which opens valve 9 and its falling edge closes valve 9. One cycle lasts 1 to 10 seconds and, preferably, about 5 seconds.

If valve 9 is located in sample line 3, the ratios described in FIG. 2 are valid for the sample flow. Accordingly, it is apparent that any desired proportion of concentration between 0% and 100% of the range of concentration of sample or reagent can be achieved in titration vessel 1 by controlling the duration of the opening and closing pulses of valve 9. The procedure and apparatus described herein permit continuous titration with only one pump. Compared with the increased technical effort required for a second pump and for the servo system for two pumps, the outlay for valve 9 and the control thereof are insignificant. Because of its simple construction, the apparatus is easy to operate and places no great demands on the operator. In addition, because of the small number of components, it is easy to service and is therefore very well suited for industrial and technological use, e.g., for the analysis of eloxation or phosphatizing baths and the like.

Although the invention has been described with reference to a preferred embodiment, some variations and modifications are possible, and it is intended that the scope of the invention be ascertained from the following claims.

We claim:

1. Apparatus for chemically analyzing a sample by fluid titration comprising:
   (a) a titration vessel;
   (b) means for sensing the titration equivalence point of the contents of the titration vessel;
   (c) a first supply line connected to a source of sample fluid and the titration vessel for supplying sample fluid to the titration vessel;
   (d) a second supply line connected to a reservoir of a reagent fluid and the titration vessel for supplying reagent fluid to the titration vessel;
   (e) means for supplying one of said sample and reagent fluids substantially continuously to said titration vessel through one of said first and second supply lines and means for supplying the other of said fluids intermittently to the titration vessel through the other of said supply lines; (f) said means for supplying the other of said fluids intermittently including valve means located in the supply line for said other fluid; and
   (g) control means connected to the valve means for controlling opening and closing of the valve means to obtain a pulse flow with the frequency and duration of the pulses providing a ratio of average sample fluid flow rate to average reagent fluid flow rate sufficient to achieve the ratio of sample fluid to reagent fluid at the equivalence point.

2. The apparatus of claim 1 wherein the valve means is located in the second supply line.

3. Apparatus for chemically analyzing a sample by titration comprising:
   (a) a titration vessel;
   (b) means for sensing the titration equivalence point of the contents of the titration vessel;
   (c) a first supply line connected to a source of sample and the titration vessel for supplying sample to the titration vessel substantially continuously;
   (d) a second supply line connected to a reservoir of a reagent and the titration vessel for supplying reagent to the titration vessel;
   (e) valve means located in said second supply line, said valve means being a three-way valve with the third outlet connected to the reservoir of reagent; and
   (f) control means connected to the valve means for controlling opening and closing of the line of the valve means between the reagent reservoir and the titration vessel to obtain a pulse flow, the frequency and duration of the pulses being such that the ratio of average sample flow rate to average reagent flow rate is sufficient to achieve the ratio of sample to reagent at the equivalence point.

4. The apparatus of claim 3 wherein the control means comprises a PID controller.

5. The apparatus of claim 4 wherein the PID controller is connected to the sensing means via a measuring transmitter and is connected to the valve means via a pulse-duration modulator.

6. The apparatus of claim 5 wherein the pulse-duration modulator is of a type which generates a pulse-shaped signal from an output signal of the PID controller and the duration of the individual pulses of the signal determines the opening and closing intervals of the valve means.

7. Apparatus for chemically analyzing a sample by titration comprising:
   (a) a titration vessel;
   (b) means for sensing the titration equivalence point of the contents of the titration vessel;
   (c) a common pump for supplying a sample and reagent to said titration vessel;
   (d) a first supply line passing through said pump and being connected to a source of sample and the titration vessel for supplying sample to the titration vessel;
   (e) a second supply line passing through said pump and being connected to a reservoir of a reagent and the titration vessel for supplying reagent to the titration vessel;
   (f) valve means located in said second supply line between said pump and said titration vessel; and
   (g) control means connected to the valve means for controlling opening and closing of the valve means to obtain a pulse flow, the frequency and duration of the pulses being such that the ratio of average sample flow rate to average reagent flow rate is sufficient to achieve the ratio of sample to reagent at the equivalence point.

8. The apparatus of claim 7 wherein the valve means comprises a first two-way valve located in the second supply line between the pump and the titration vessel and a second two-way valve located in a branch of the second supply line which is connected to the reservoir of the reagent.

9. The apparatus of claim 7 wherein the valve means is a three-way valve with the third outlet connected to the reservoir of the reagent.

10. The apparatus of claim 9 wherein the control means comprises a PID controller.

11. The apparatus of claim 10 wherein the PID controller is connected to the sensing means via a measuring transmitter and is connected to the valve means via a pulse-duration modulator.

12. The apparatus of claim 11 wherein the pulse-duration modulator is of a type which generates a pulse-shaped signal from an output signal of the PID controller and the duration of the individual pulses of the signal determines the opening and closing intervals of the valve means.

13. Continuous titration apparatus for chemically analyzing a liquid, comprising a titration vessel, supply means for supplying to said titration vessel liquid to be analyzed and titration reagent liquid, said supply means supplying one of the liquids to said titration vessel at a substantially constant rate and including valve means which may be opened to allow flow of the other of the liquids to said titration vessel and which may be closed to block such flow, means for sensing the titration equivalence point of the contents of said titration vessel, and control means operatively connected both to said means for sensing the titration equivalence point of the contents of said titration vessel and to said valve means for pulsing said valve means to control average rate of flow through said valve means.

14. Continuous titration apparatus for chemically analyzing a flowing liquid by addition of a flow of titration reagent thereto, comprising a titration vessel in which the flowing liquid to be analyzed and the flow of titration reagent are mixed; supply means for supplying to said titration vessel liquid to be analyzed at a first average flow rate and for supplying to said titration vessel a titration reagent at a second average flow rate; means for sensing the titration equivalence point of the contents of said titration vessel; and means for controlling at least one of said first and second average flow rates, said means for controlling at least one of said first and second average flow rates including valve means which may be opened to allow flow to said titration vessel and which may be closed to block such flow, and means operatively connected both to said means for sensing the titration equivalence point of the contents of said titration vessel and to said valve means for pulsing said valve means to control average rate of flow through said valve means.

15. Continuous titration apparatus according to claim 14, wherein said titration vessel has a predetermined volume, wherein said titration vessel is provided with an overflow outlet, and wherein said means for pulsing said valve means regulates the length of time when said valve means is in the open state thereof and limits the volume flowing to said titration vessel during each pulse to less than about one-tenth of said titration vessel volume.

16. Continuous titration apparatus for chemically analyzing a liquid, comprising a titration vessel, supply means for supplying a liquid to be analyzed to said titration vessel at a substantially constant rate and for supplying a pulsed flow of titration reagent to said titration vessel, said supply means including valve means which may be opened to allow flow of titration reagent to said titration vessel and which may be closed to block such flow, means for sensing the titration equivalence point of the contents of said titration vessel, and control means operatively connected both to said means for sensing the titration equivalence point of the contents of said titration vessel and to said valve means for causing pulsing of said valve means between the open and closed states thereof to control the average rate of flow of titration reagent through said valve means.

* * * * *